(12) United States Patent
Buchanan et al.

(10) Patent No.: US 11,984,677 B2
(45) Date of Patent: *May 14, 2024

(54) PRINTED CIRCUIT BOARD CABLE CLIP FOR SIGNAL SENSITIVE APPLICATIONS

(71) Applicant: WEST AFFUM HOLDINGS DAC, Dublin (IE)

(72) Inventors: Robert R. Buchanan, Bothell, WA (US); Douglas K. Medema, Everett, WA (US); Daniel R. Piha, Bellevue, WA (US); Dallas E. Meeker, Kirkland, WA (US); Daniel J. Finney, Woodinville, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 32 days.

This patent is subject to a terminal disclaimer.

(21) Appl. No.: 17/372,945

(22) Filed: Jul. 12, 2021

(65) Prior Publication Data

US 2022/0006211 A1 Jan. 6, 2022

Related U.S. Application Data

(63) Continuation of application No. 16/812,265, filed on Mar. 6, 2020, now Pat. No. 11,063,378.

(Continued)

(51) Int. Cl.
*H01R 12/53* (2011.01)
*A61N 1/39* (2006.01)
(Continued)

(52) U.S. Cl.
CPC ........... *H01R 12/53* (2013.01); *A61N 1/3904* (2017.08); *H01R 4/027* (2013.01); *H05K 1/111* (2013.01); *H05K 2201/10356* (2013.01)

(58) Field of Classification Search
CPC .......... H05K 2201/10356; H05K 1/111; A61N 1/3904; H01R 4/027; H01R 4/02; H01R 12/53
(Continued)

(56) References Cited

U.S. PATENT DOCUMENTS

| 3,724,455 A | 4/1973 | Unger |
| 4,583,524 A | 4/1986 | Hutchins |

(Continued)

FOREIGN PATENT DOCUMENTS

| EP | 3380189 B1 | 10/2018 |
| WO | 1998039061 A2 | 9/1998 |
| WO | 2012064604 A1 | 5/2012 |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

(Continued)

*Primary Examiner* — Tremesha S Willis
(74) *Attorney, Agent, or Firm* — Columbia IP Law

(57) ABSTRACT

Technologies and implementations for a clip to connect coaxial cables onto a printed circuit board assembly (PCBA) are disclosed. The technologies and implementations facilitate improved signal integrity from the cable to various components of the PCBA. Additionally, the technologies and implementations help facilitate management of mechanical variations during connection of the coaxial cable.

17 Claims, 6 Drawing Sheets

Related U.S. Application Data

(60) Provisional application No. 62/815,283, filed on Mar. 7, 2019.

(51) Int. Cl.
*H01R 4/02* (2006.01)
*H05K 1/11* (2006.01)

(58) Field of Classification Search
USPC .......................................................... 174/250
See application file for complete search history.

(56) References Cited

U.S. PATENT DOCUMENTS

| | | |
|---|---|---|
| 4,619,265 A | 10/1986 | Morgan et al. |
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,618,208 A | 4/1997 | Crouse et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Lyster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Inder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 3/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,676,313 B2 | 3/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,482,820 B1 * | 11/2016 | Barwicz ............... G02B 6/3893 |
| 9,592,403 B2 | 3/2017 | Sullivan |
| 9,878,171 B2 | 1/2018 | Kaib |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2006/0173499 A1 | 8/2006 | Hampton et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0012144 A1 | 1/2014 | Crone |
| 2014/0025131 A1 | 1/2014 | Sullivan et al. |
| 2014/0046391 A1 | 2/2014 | Cowan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |

OTHER PUBLICATIONS

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

Metting Van Rijn, A. C., Peper A., & Grimbergen, C. A., High-Quality Recording of Bioelectric Events Part 1: Interference Reduction, Theory and Practice, Review, Medical & Biological Engineering & Computing, Sep. 1990, pp. 389-397, IFMBE.

Pagan-Carlo, et al., "Encircling Overlapping Multipulse Shock Waveforms for Transthoracic Defibrillation," JACC Journals, Dec. 1998, vol. 32 Issue 7, p. 2065-2071.

* cited by examiner

PRINTED CIRCUIT BOARD CABLE CLIP FOR SIGNAL SENSITIVE APPLICATIONS

RELATED APPLICATION

This application is a continuation application of U.S. patent application Ser. No. 16/812,265, filed on Mar. 6, 2021, titled PRINTED CIRCUIT BOARD CABLE CLIP FOR SIGNAL SENSITIVE APPLICATIONS now U.S. Pat. No. 11,063,378 and claims benefit of priority to U.S. Provisional Patent Application Ser. No. 62/815,283, filed on Mar. 7, 2019, titled PCBA WITH COAXIAL CABLES CONNECTED VIA SPECIAL CLIPS AND METHODS, both of which are incorporated herein by reference in their entirety for all purposes.

INFORMATION

Wires are utilized in various technologies. Wires are capable of carrying signals (e.g., electrical signal and/or data signal). Some wires may be used in technologies involving sensitive signals such as, but not limited to, healthcare device technologies. One example of a healthcare device technology may be defibrillator technology. Maintaining integrity of the signals carried by the wires utilized in defibrillator technology may be relevant. Accordingly, wires utilized in defibrillator technology may be employed managing various concerns with the signal.

An example of wires utilized in defibrillator technology may include wires utilized in wearable cardioverter defibrillator (WCD) systems. Wires utilized in WCD systems may include various structures to facilitate maintenance of signal integrity. For example, the wires utilized in WCD systems may include various wires such as, but not limited to, an electrocardiogram (ECG) cable. Besides a metal wire, an ECG cable may include various structures to help facilitate maintenance of signal integrity such as, but not limited to, a coaxial cable. One example of a structure may include various construction such as, but not limited to, a triaxial construction. The triaxial construction may include a center conductor (e.g., metal wire), a first insulation layer, an inner shield layer, a second insulation layer, an outer shield, and a jacket. The various layers of the triaxial construction help facilitate maintenance of signal integrity (e.g., high quality ECG signal measurement in a WCD system).

The cable may commonly provide signals to various signal processing electronic components. The electronic components may be deployed on a printed circuit board (PCB). Accordingly, the cable may be communicatively coupled to the PCB to provide the signals to the electronic components for various processing forming a PCB assembly (PCBA).

The cable may be soldered to the PCB by hand or utilize a relatively long clip connection for an electrical connection. Both of these methodologies may be prone to damage the cable due to heat effects of the solder melting through some of the layers of the cable (e.g., inner insulator layer). Additionally, insulator layers may be relatively sensitive to heat effects due to the dielectric material being selected to minimizing triboelectric noise, which may be generated during cable movement. For example, low triboelectric noise materials may have relatively low thermal softening temperatures, which may make them susceptible to melting and displacement when heat is applied to the shield layers for soldering. Melting and displacement may result in some manufacturing defects due to the shield layers either shorting together or shorting with the center conductor when excessive heat was applied causing the insulation layers to melt and be displaced. Additionally, the process of soldering directly to the PCB pads required manual operations to spindle up the woven or twisted shield conductors into a single braid that could be soldered to the pad, which may be very time consuming and subject to inconsistencies based on the skill of an assembly operator.

SUMMARY

Described herein are various illustrative apparatus for conductive clips. Example apparatus may include a cable connecting clip. The cable connecting clip may include a channel that may be configured to receive a cable having a structure. The channel may be shaped to fit the cable. The cable connecting clip may have a saddle section having a first flange and a second flange on the opposite sides of the channel. The flanges may be configured to guide the cable into the channel. A connecting pad section may be disposed on the cable connecting clip and may be configured to couple a conductive layer of the cable to the clip.

The present disclosure also describes a printed circuit board assembly (PCBA) system that may include a cable having a signal conductor and at least a first conductive layer. The PCBA may include a substrate having at least a first and second conductive regions. The PCBA may also include a first conductive clip having a pad section, a saddle section, and a neck section connected between the pad and saddle sections, the neck section being narrower than the pad and saddle sections. The portion of the cable may be disposed in the saddle section of the first conductive clip, and a portion of the first conductive layer of the cable is soldered to the saddle section of the first conductive clip. Additionally, the pad section of the first conductive clip is soldered to the first conductive region of the substrate to electrically connect the portion of the first conductive layer of the cable to the first conductive region of the substrate, and the signal conductor of the shielding cable is soldered to the second conductive region of the substrate.

In some examples, subject matter of the present disclosure may be applicable to wearable cardioverter defibrillator (WCD) system having a PCBA with clips.

The foregoing summary is illustrative only and not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

In the drawings.

DETAILED DESCRIPTION

Figure 1:
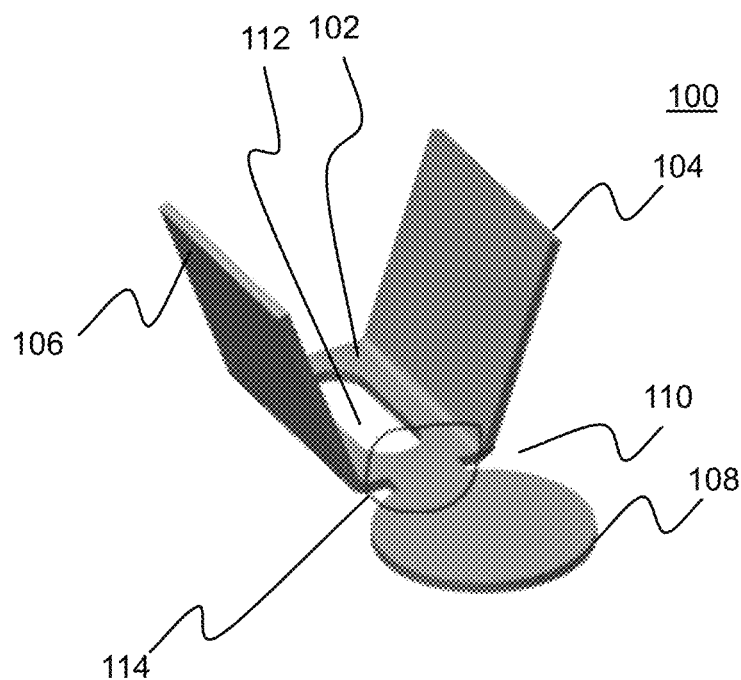
FIG. 1 illustrates a cable connecting clip in accordance with various embodiments.

The following description sets forth various examples along with specific details to provide a thorough understanding of claimed subject matter. It will be understood by those skilled in the art, however, that claimed subject matter may be practiced without some or more of the specific details disclosed herein. Further, in some circumstances, well-known methods, procedures, systems, components and/or circuits have not been described in detail in order to avoid unnecessarily obscuring claimed subject matter.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

This disclosure is drawn, inter alia, to apparatus, and systems related to a providing an improved cable connection system for a printed circuit board assembly (PCBA).

Various cables may be utilized in various applications. A cable may carry various electrical signals. The electrical signals may be processed by various electronic components. In order to facilitate processing of the electrical signals by the electronic components, the cables may be communicatively coupled to the electronic components by various connections. The connections may be facilitated by a connection of the cable to an electronic component platform such as, but not limited to, a printed circuit board (PCB). The PCB may have various communicative connections (e.g., electrical lines and/or vias). In turn, the communicative connections may be connected to the electrical components for processing. Accordingly, the manner with which the cable connects to the PCB may be relevant to signal integrity received by the electronic components via the cable.

Before turning to the figures, a non-limiting example application of the various embodiments of the present disclosure may be described. In the non-limiting example, a signal communicating cable may be utilized in healthcare technology such as, but not limited to, defibrillator technology, where signal integrity may be relevant (e.g., noise-sensitivity). An example of a cable utilized in defibrillator technology may be a cable utilized in wearable cardioverter defibrillator (WCD) systems. In order to manage and increase the signal integrity of electrocardiogram (ECG) signals in WCD applications, cables having various structures may be employed. One example of a cable structure may include a biaxial structure, which may have a center conductor (e.g., a metal wire), which may typically carry the noise-sensitive signal (e.g., ECG signal), an insulator layer, which may be made from dielectric material surrounding the center conductor, a conductive shield (commonly, braid-like), which may surround the insulator layer, and a final insulator layer, which may surround the conductive shield. Another example of a cable structure may include a triaxial cable structure having a center conductor (e.g., a metal wire), which may typically carry the noise-sensitive signal (e.g., ECG signal), an inner insulator layer, which may be made from dielectric material surrounding the center conductor, an inner conductive shield (commonly, braid-like), which may surround the inner insulator layer, an outer conductive shield (commonly, braid-like), which may surround the outer insulator layer, and a final insulator layer, which may surround the outer conductive shield. The utilization of the structure of the cable may be based, at least in part, on the application of the cable and the sensitivity of the application to signal noise and/or integrity. For the purposes of the present non-limiting example, the structure of the cable may be determined to be triaxial as described above.

Continuing with the non-limiting example of a cable having a triaxial structure utilized in WCD system applications, at least one end of the cable may be communicatively coupled to a PCB to facilitate processing of the ECG signal to and/or from the cable. In order to communicatively couple the cable to the PCB, the various layers of the cable may be stripped back to expose the various layers (e.g., center conductor, insulator layers, and conductive shield layers). The stripped back cable may then be soldered onto the PCB forming a PCB assembly.

In the non-limiting example, a wire connecting clip may be disposed on the PCB. The clip may be soldered onto the PCB and be a predetermined distance from a conductive signal pad such as, but not limited to, a substantially flat landing pad. The clip may be communicatively coupled to various electronic components on the PCB (also referred herein as a PCB assembly or PCBA). The clip may be communicatively coupled to the PBC by being soldered onto one or more signal lines in various conductive regions of the PCB.

Continuing with the non-limiting example of an ECG cable utilized with a WCD, the stripped back cable (e.g., exposing predetermined lengths of the various layers of the structure of the cable) may be disposed into the clip. The clip may have flanges to guide the cable into a channel of the clip substantially seating the cable into the clip. While the cable is soldered to the clip, the clip may facilitate holding of the cable in its position within the channel. The position of the clip may be on the PCB to facilitate accurate placement of the cable.

For example, the center conductor, which may facilitate communication of a signal (i.e., signal conductor), may be communicatively coupled (e.g., soldered) to a conductive signal pad such as, but not limited to, a flat landing pad. The clip may be positioned a predetermined distance from the landing pad. The cable may be stripped to expose the various layers of the structure corresponding to the predetermined distance. Accordingly, the stripped cable may be placed into the clip, the cable may be soldered to the clip, the center conductor may be positioned on the landing pad, and the center conductor may be soldered to the landing pad. Because the clip may facilitate accurate positioning of the cable (i.e., the various exposed layers), the process of stripping the cable, placement of the cable onto the PCB, and soldering the cable onto the PCB may at least partially or in any combination be substantially automated. Additionally, the clip may help facilitate envelopment of the shield layers with solder without the application of significant amount of force resulting in facilitation of prevention of melting and displacement of the insulation layers of the cable. Further, the clip may have various features, including selection of materials, to help facilitate compensation of the mechanical effects of the soldering process (e.g., dimensional changes due to heat, heat dissipation, heat isolation controlling the spread of heat to various parts of the cable and its structures, etc.).

Turning now to the figures, FIG. 1 illustrates a cable connecting clip in accordance with various embodiments. Shown in FIG. 1, a cable connecting clip 100 may include a channel 102, a first flange 104, a second flange 106, and a connecting pad 108. The channel 102 may be configured to receive a cable 202 (shown in FIG. 2) with the channel 102 having a shape to substantially fit the cable 202. As shown, the first flange 104 and the second flange 106 may be disposed on opposite sides of the channel and be configured to guide the cable 202 into the channel 102. The connecting pad 108 may be disposed on an end 110 of the channel 102. Additionally, the connecting pad 108 may be configured to couple a conductive layer 212 (shown in FIG. 2) of the cable 202 to the clip 100.

Continuing to refer to FIG. 1, in the example shown in FIG. 1, the channel 102 may include a thermal mechanical compensating structure 112. The thermal mechanical compensating structure 112 may be in the form of a slot having a predetermined dimension to manage mechanical stresses that may be imparted on the clip 100 due to heat from soldering (e.g., twisting, expansion, swelling, etc.). Additionally, between the connecting pad 108 and the channel 102, a heat transfer management structure 114 may be present. In the example shown in FIG. 1, the heat transfer management structure 114 may in the form of a neck (i.e., a narrow thermal path) between the channel 102 and the connecting pad 108. It should be appreciated that even though the thermal mechanical compensating structure 112 and the heat transfer management structure 114 may be in the form of a slot and a neck respectively, the thermal mechanical compensating structure 112 and the heat transfer management structure 114 may be in a variety of forms and structures. For example, the thermal mechanical compensating structure 112 may be in the form of a hole, an ellipse, a solid of the same material, a solid of a different material, a rectangular hole, etc. and any combination thereof. Additionally, the heat transfer management structure 114 may be in a variety of forms such as, but not limited to, a wire, solid material, hybrid material, a gap, etc. and any combination thereof.

In the example shown in FIG. 1, the first flange 104 and the second flange 106 may substantially form a "V" type shape to guide the cable 202, in particular the conductive layer 212 of the cable 202, into the channel 102. As will be shown, the first flange 104 and the second flange 106 may form a variety of shapes to help guide the cable 202 into the channel. Additionally, the first flange 104 and the second flange 106 may be configured to help facilitate holding the cable 202 in place. For example, the first flange 104 and the second flange 106 may help guide the cable 202 into the channel 102 and help to hold the cable 202 within the channel 102 by a pinching action on the cable 202. For example, the channel 102, the first flange 104, and the second flange 106 may collectively act as a clip holding the cable 202 in place during and after soldering.

It is contemplated within the subject matter of the disclosure that the clip 100 may be made from a variety of material such as, but not limited to, metals. Some examples of metals may include tin, cadmium, gold, silver, palladium, rhodium, copper, bronze, brass, lead, nickel silver, beryllium copper, carbon steel, low alloy steel, zinc, nickel, aluminum, aluminum bronze, high alloy steels, stainless steel, cast iron, chromium, titanium, tantalum, magnesium, etc., and any combination thereof. Additionally, the clip may be made of a variety of polymer material such as, but not limited to, carbon materials. Some examples of carbon materials may include carbon fibers, carbon nanotube fibers, carbon-carbon combinations, carbon-metal combinations, etc., and any combination thereof.

It should be noted that the clip 100 may also be referred to as a conductive clip, and accordingly, the terms clip and conductive clip may be used interchangeably. Additionally, the combination of the features the first flange 104, the second flange 106, and the channel 102 may be referred together as a saddle, and accordingly, the term saddle may refer to the combination of features as described.

Figure 2:
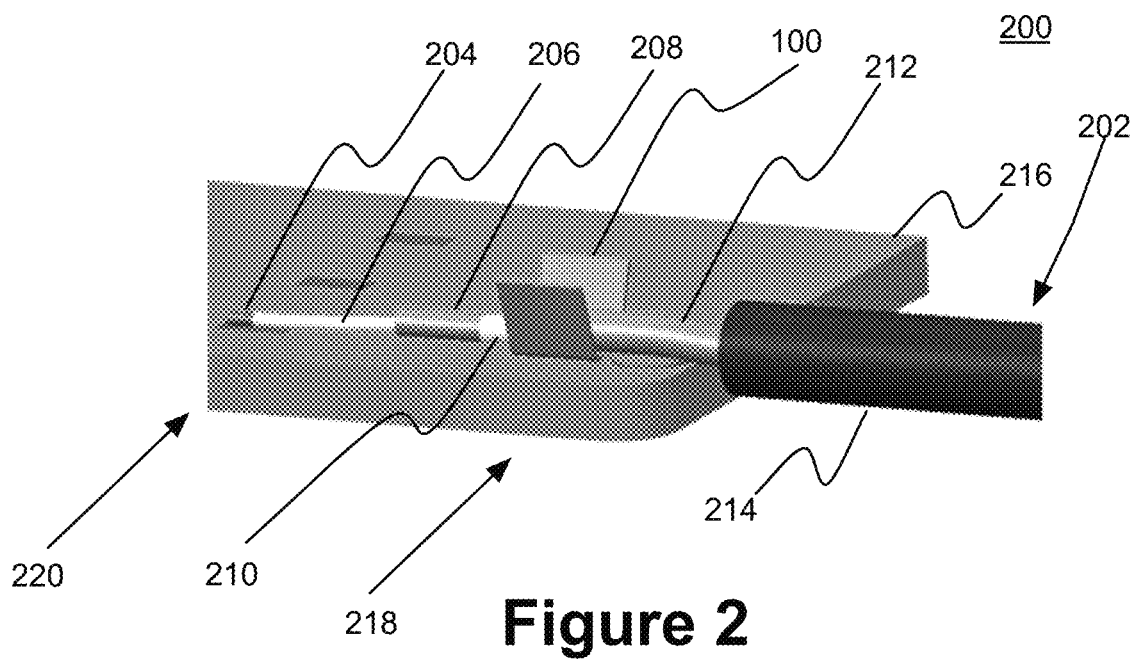
FIG. 2 illustrates a clip as may be utilized in accordance with various embodiments of the disclosure.

FIG. 2 illustrates a clip 100 (shown in FIG. 1) as may be utilized in accordance with various embodiments of the disclosure. In FIG. 2, a printed circuit board assembly (PCBA) system 200 may include the clip 100, which may be disposed on a printed circuit board (PCB) 216. The PCB 216 may have a first conductive region 218 and a second conductive region 220, where the clip 100 may be disposed on the first conductive region 218 of the PCB 216 (i.e., on a substrate of the PBC 216). As shown, the clip 100 may be configured to receive the cable 202.

The cable 202 may have a predetermined structure as previously described. In FIG. 2, the cable 202 may be of a coaxial type such as, but not limited to, a triaxial type cable. Accordingly, in the example illustrated in FIG. 2, the cable 202 may have a center conductor 204, an inner insulator layer 206, an inner conductive shield 208, an outer insulator layer 210, an outer conductive shield 212, and a final insulator layer 214. As shown in FIG. 2, the cable 202 may be stripped back exposing the various layers 204, 206, 208, 210, and 212. The lengths of the stripping may be based, at least in part, on the proximate locations of the conductive regions 218 and 220. For example, a portion of the cable 202 (e.g., the outer conductive shield 212) may be disposed in the saddle section of the conductive clip 100. The outer conductive shield 212 portion may be soldered to the saddle section of the clip 100. The pad section 108 (shown in FIG. 1) may be soldered to the first conductive region 218 of the PCB 216, thereby causing an electrical connection between the first conductive region 218 of the PCB 216 and the outer conductive shield 212 of the cable 202. The center conductor 204 (i.e., signal conductor) of the cable 202 may be soldered to the second conductive region 220 of the PCB 216.

As shown in FIG. 2, the clip 100 may help to facilitate accurate placement of the cable 202 in its appropriate position on the PCB 216 (e.g., accurately hold the layers 204, 206, 208, 210, and 212 of the cable 202 in their correct positions for proper connection with the PCBA 200). Additionally, the clip 100 may help facilitate envelopment of the shield layers 204, 206, 208, 210, and 212 of the cable 202 with solder without the application of significant amount of force resulting in facilitation of prevention of melting and displacement of the insulation layers 204, 206, 208, 210, and 212 of the cable 202. Further, as described with respect to FIG. 1, the clip 100 may have various features (geometric and/or selection of materials) to help facilitate compensation of the mechanical effects of the soldering process (e.g., dimensional changes due to heat, heat dissipation, heat isolation controlling the spread of heat to various parts of the cable and its structures, etc.).

Figure 3:
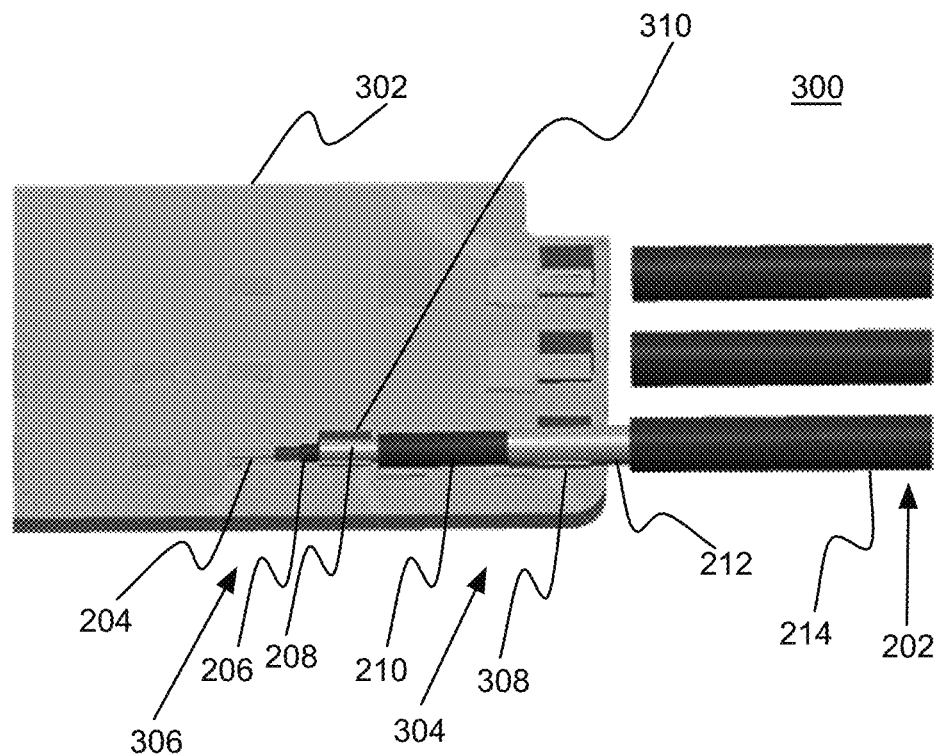
FIG. 3 illustrates a printed circuit board assembly (PCBA) utilizing more than one clip, in accordance with various embodiments.

FIG. 3 illustrates a PCBA utilizing more than one clip, in accordance with various embodiments. In FIG. 3, a PCBA 300 may have a first conductive region 304 and a second conductive region 306 on the PCB 302. Disposed on the first conductive region 304 may be a first clip 308, and on the second conductive region 306, may be a second clip 310. As shown, the first clip 308 may hold the outer conductive shield 212 of the cable 202 in its saddle section. The second clip 310 may hold the inner conductive shield 208 of the cable 202. As previously described, the first and second clips 308 and 310 may be soldered via pad sections to the first and second conductive regions 304 and 306 of the PCB 302. Again, there may be various design desirability that may be relevant to the number of clips utilized in the PCBA 300 including the previously described mechanical concerns.

Figure 4:
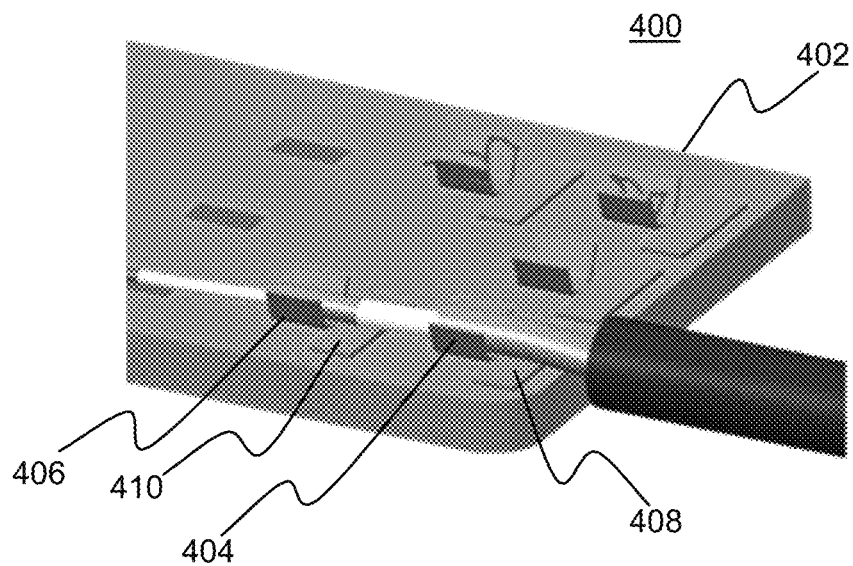
FIG. 4 illustrates one or more clips on a PCBA, in accordance with various embodiments.

FIG. 4 illustrates one or more clips on a PCBA, in accordance with various embodiments. In FIG. 4, the PCBA 400 may include a PCB 402, and disposed on the PCB 402 may be a first clip 404 and a second clip 406. As shown, the first clip 404 may have a first connecting pad 408, and the second clip 406 may have a second connecting pad 410. As shown in FIG. 4, the first and second clips 404 and 406 may be oriented with each other in a variety of manners such as in line with each other (as shown) or opposing each other (as shown in FIG. 3). Accordingly, it is contemplated within the scope of the claimed subject matter that the clips 404 and 406 may be oriented in a variety of manners on the PCB 402 such as, but not limited to various angular orientations (e.g., 90 degrees, 45 degrees, etc.).

Figure 5:
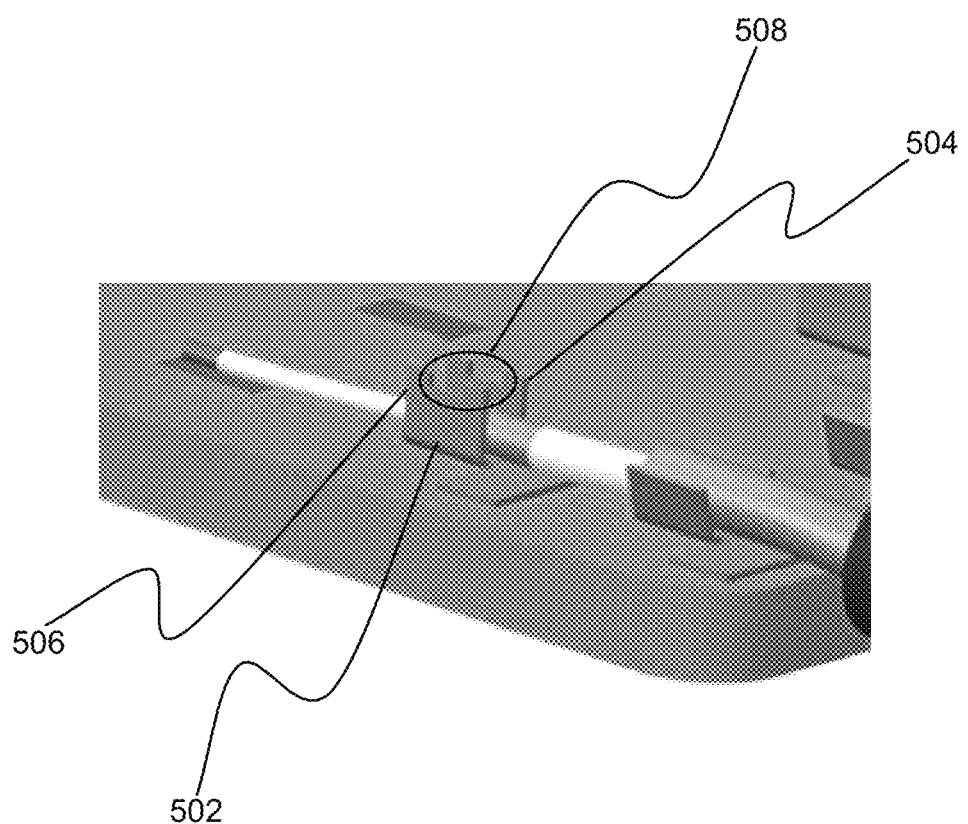
FIG. 5 illustrates a clip, in accordance with another embodiment.

FIG. 5 illustrates a clip, in accordance with another embodiment. In FIG. 5, a clip 502 may have a first flange 504 and a second flange 506 having a geometric feature such as, but not limited to, a cutout 508. The cutout 508 may help to facilitate improved soldering of the cable including facilitating automation. The cutout may have a variety of shapes and sizes based, at least in part, on the mechanical concerns of this area of the saddle section. Additionally, the cutout may help facilitate compensation of mechanical stresses and/or issues as some examples have been described previously.

Figure 6A:
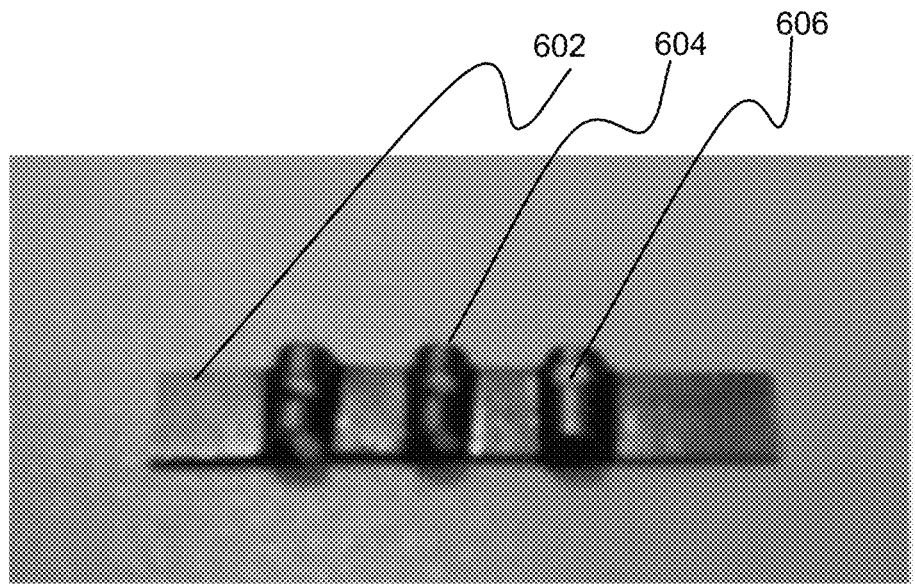
FIGS. 6A and 6B illustrate a clip, in accordance with another embodiment.
Figure 6B:
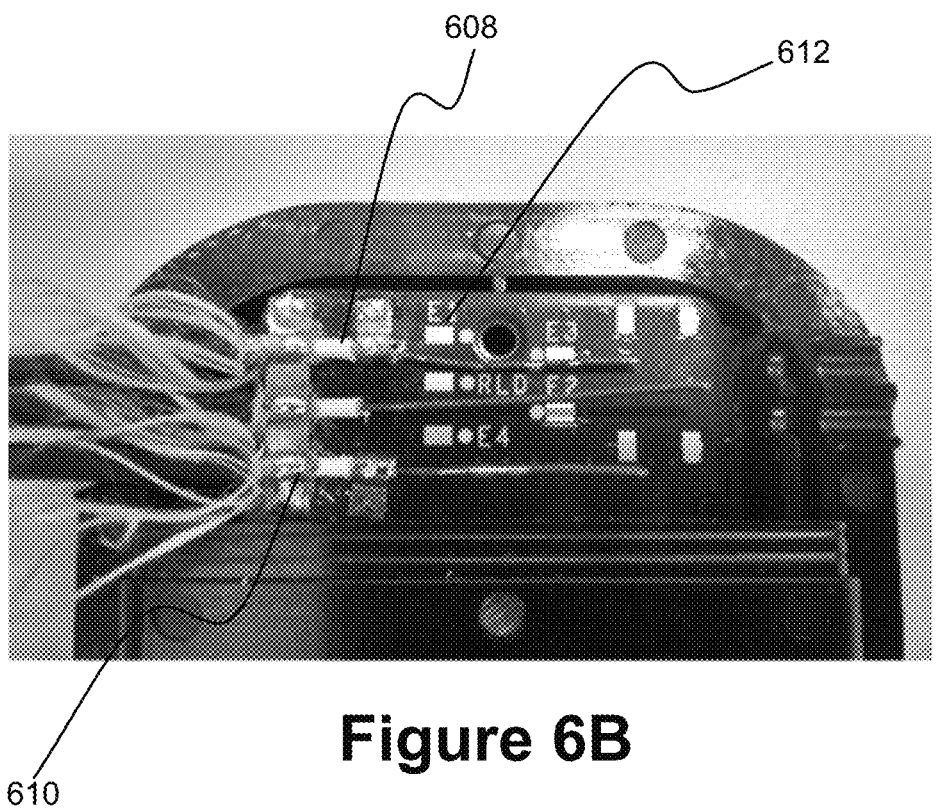

FIGS. 6A and 6B illustrate a clip, in accordance with another embodiment. Shown in FIGS. 6A and 6B, a clip 602 may be in the form of a bracket having a curved channel 604 configured to accommodate a cable 608, and a solder hole 606. The curved channel 604 may be shaped to hold a section of the cable 608. The solder hole 606 may facilitate placement of a solder 610 to hold the cable 608 in place and conductively connect the cable to a PCB 612.

Figure 7:
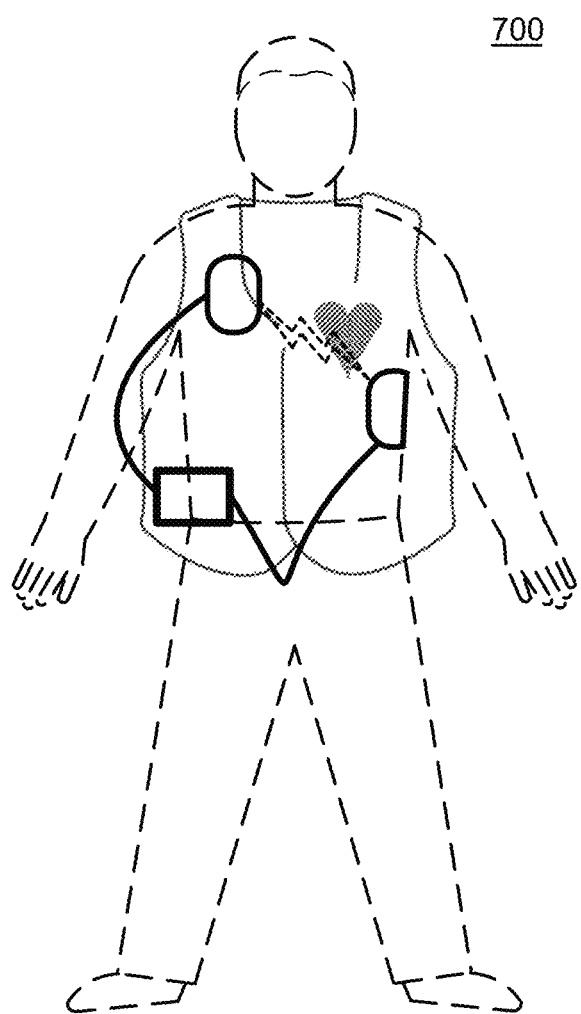
FIG. 7 illustrates an example application of a clip, in accordance with various embodiments.

FIG. 7 illustrates an example application of a clip, in accordance with various embodiments. In FIG. 7, a wearable cardioverter defibrillator (WCD) system 700 is shown.

Figure 8:
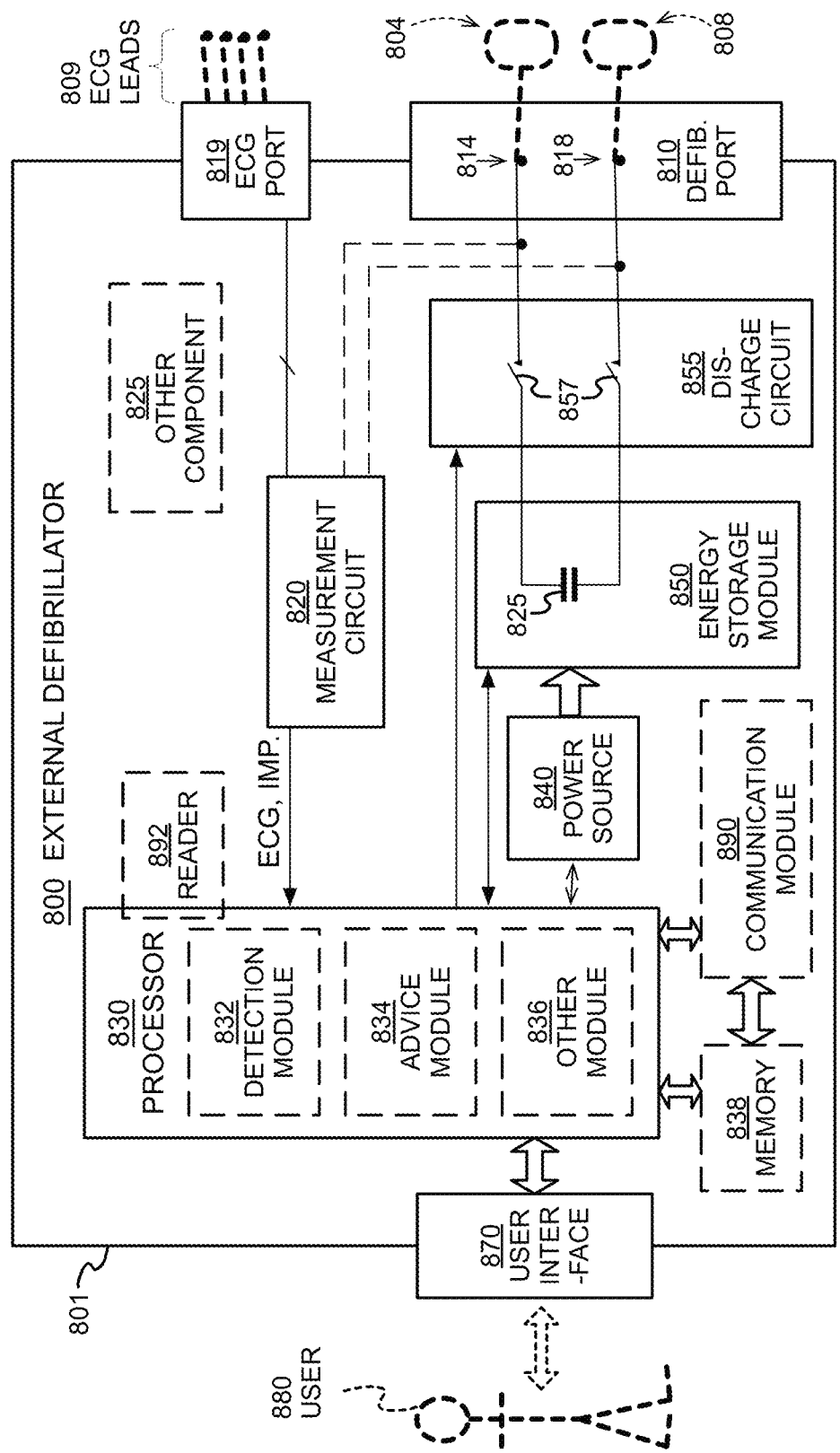
FIG. 8 is a block diagram illustrating components of defibrillator device, which may be used with various embodiments.

FIG. 8 is a block diagram illustrating components of a defibrillator device, which may be used with various embodiments. These components may be, for example, a WCD 700 (shown in FIG. 7).

The defibrillator device 800 may be intended for use by a user 880 (e.g., a wearer). The defibrillator device 800 may typically include a defibrillation port 810, such as a socket in housing 801. The defibrillation port 810 may include nodes 814 and 818. One or more electrodes 804 and 808, which may be plugged into the defibrillation port 810, so as to make electrical contact with nodes 814 and 818, respectively. It may also be possible that the electrodes 804 and 808 may be connected continuously to the defibrillation port 810, etc. Either way, the defibrillation port 810 may be used for guiding via the electrodes 804 and 808 to a person (see FIG. 7) an electrical charge that may have been stored in the defibrillator device 800, as described herein.

The defibrillator device 800 may also have an ECG port 819 in the housing 801, for receiving ECG cables 809. The ECG cables 809 may facilitate sensing of an ECG signal (e.g., a 12-lead signal or from a different number of lead signals). Moreover, a defibrillator-monitor could have additional ports (not shown), and the other component 825 may be configured to filter the ECG signal (e.g., application of at least one filter to the signal to help facilitate removal of artifacts such as, but not limited to, chest compression due to chest compressions being delivered to the person).

The defibrillator 800 also may include a measurement circuit 820. The measurement circuit 820 may receive physiological signals from the ECG port 819, and also from other ports, if provided. The circuit 820 may render detected physiological signals and their corresponding information. The information may be in the form of data, or other signals, etc.

If the defibrillator 800 is configured as a WCD type device, ECG port 819 may not be present. The measurement circuit 820 may obtain physiological signals through the nodes 814 and 818 instead, when the electrodes 804 and 808 are attached to the person (see FIG. 7). In these cases, a person's ECG signal may be detected as a voltage difference between the electrodes 804 and 808. Additionally, the impedance between the electrodes 804 and 808 may be detected, among other things, whether the electrodes 804 and 808 have been inadvertently disconnected from the person.

The defibrillator 800 may also include a processor 830. The processor 830 may be implemented in a wide variety of manners for causing actions and operations to be performed. Some examples may include digital and/or analog processors such as microprocessors and digital-signal processors (DSPs), controllers such as microcontrollers, software running in a machine environment, programmable circuits such as Field Programmable Gate Arrays (FPGAs), Field-Programmable Analog Arrays (FPAAs), Programmable Logic Devices (PLDs), Application Specific Integrated Circuits (ASICs), and so on or any combination thereof.

The processor 830 may include a number of modules. One example module may be a detection module 832, which may detect outputs from the measurement circuit 820. The detection module 832 may include a VF detector. Accordingly, the person's detected ECG may be utilized to help determine whether the person is experiencing ventricular fibrillation (VF).

In another example module may be an advice module 834, which may provide advice based, at least in part, on outputs of detection module 832. The advice module 834 may include an algorithm such as, but not limited to, Shock Advisory Algorithm, implement decision rules, and so on. For example, the advice may be to shock, to not shock, to administer other forms of therapy, and so on. If the advice is to shock, some defibrillator examples may report the advice to the user, and prompt them to do it. In other examples, the defibrillator device may execute the advice by administering the shock. If the advice is to administer CPR, the defibrillator 800 may further issue prompts for administrating CPR, and so forth.

The processor 830 may include additional modules, such as module 836 for various other functions. Additionally, if other component 825 is provided, it may be operated in part by processor 830, etc.

In an example, the defibrillator device 800 may include a memory 838, which may work together with the processor 830. The memory 838 may be implemented in a wide variety of manners. For example, the memory 838 may be implemented such as, but not limited to, nonvolatile memories (NVM), read-only memories (ROM), random access memories (RAM), and so forth or any combination thereof. The memory 838 may can include programs for the processor 830, and so on. The programs may include operational programs execution by the processor 830 and may also include protocols and methodologies that decisions may be made by advice module 834. Additionally, the memory 838 may store various prompts for the user 880, etc. Moreover, the memory 838 may store a wide variety of information (i.e., data) such as, but not limited to information regarding the person.

The defibrillator 800 may also include a power source 840. In order to facilitate portability of defibrillator device 800, the power source 840 may include a battery type device. A battery type device may be implemented as a battery pack, which may be rechargeable or not be rechargeable. At times, a combination of rechargeable and non-rechargeable battery packs may be utilized. Examples of power source 840 may include AC power override, where AC power may be available, and so on. In some examples, the processor 830 may control the power source 840.

Additionally, the defibrillator device 800 may include an energy storage module 850. The energy storage module 850 may be configured to store some electrical energy (e.g., when preparing for sudden discharge to administer a shock). The energy storage module 850 may be charged from the power source 840 to an appropriate level of energy, as may be controlled by the processor 830. In some implementations, the energy storage module 850 may include one or more capacitors 852, and the like.

The defibrillator 800 may include a discharge circuit 855. The discharge circuit 855 may be controlled to facilitate discharging of the energy stored in energy storage module 850 to the nodes 814 and 818, and also to electrodes 804 and 808. The discharge circuit 855 may include one or more switches 857. The one or more switches 857 may be configured in a number of manners such as, but not limited to, an H-bridge, and so forth.

The defibrillator device 800 may further include a user interface 870 for the user 880. The user interface 870 may be implemented in a variety of manners. For example, the user interface 870 may include a display screen capable of displaying what is detected and measured, provide visual feedback to the user 880 for their resuscitation attempts, and so forth. The user interface 870 may also include an audio output such as, but not limited to, a speaker to issue audio prompts, etc. The user interface 870 may additionally include various control devices such as, but not limited to, pushbuttons, touch display, and so forth. Additionally, the discharge circuit 855 may be controlled by the processor 830 or directly by the user 880 via the user interface 870, and so forth.

Additionally, the defibrillator device 800 may include other components. For example, a communication module 890 may be provided for communicating with other machines and/or the electrodes. Such communication may be performed wirelessly, or via wire, or by infrared communication, and so forth. Accordingly, information may be communicated, such as person data, incident information, therapy attempted, CPR performance, ECG information, and so forth.

It should be appreciated that it is contemplated within the scope and spirit of the present disclosure that the claimed subject matter may include a wide variety of clips, materials, mechanical shapes, etc. Accordingly, the claimed subject matter is not limited in these respects.

In some portions of the description, illustrative implementations of the disclosure may have been described with reference to the elements of the components described with respect to FIGS. 1-8. However, the described embodiments are not limited to these depictions. More specifically, some elements/components depicted in FIGS. 1-8 may be omitted from some implementations detailed herein. Furthermore, other elements not depicted in FIGS. 1-8 may be used to implement example apparatuses detailed herein.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Reference in the specification to "an implementation," "one implementation," "some implementations," or "other implementations" may mean that a particular feature, structure, or characteristic described in connection with one or more implementations may be included in at least some implementations, but not necessarily in all implementations. The various appearances of "an implementation," "one implementation," or "some implementations" in the preceding description are not necessarily all referring to the same implementations.

While certain exemplary techniques have been described and shown herein using various methods and systems, it should be understood by those skilled in the art that various other modifications may be made, and equivalents may be substituted, without departing from claimed subject matter. Additionally, many modifications may be made to adapt a particular situation to the teachings of claimed subject matter without departing from the central concept described herein. Therefore, it is intended that claimed subject matter not be limited to the particular examples disclosed, but that such claimed subject matter also may include all implementations falling within the scope of the appended claims, and equivalents thereof.

What is claimed:

1. A cable connecting clip included in a wearable cardioverter defibrillator (WCD), the cable connecting clip comprising:
    a channel configured to receive an electrode cable being of a predetermined structure, the channel having a shape to substantially fit the electrode cable;
    a first flange and a second flange disposed on opposite sides of the channel, the first flange and the second flange configured to guide the electrode cable into the channel; and
    a connecting pad disposed on an end of the channel, the connecting pad configured to couple a conductive layer of the electrode cable to the cable connecting clip to couple the electrode cable with the WCD.

2. The cable connecting clip of claim 1, wherein the channel comprises a thermal mechanical compensating structure.

3. The cable connecting clip of claim 2, wherein the thermal mechanical compensating structure comprises a slot, the slot having a predetermined dimension to compensate for thermal mechanical changes of the cable connecting clip.

4. The cable connecting clip of claim 1, wherein the first flange and the second flange comprise the first flange and the second flange forming a substantially "V" type shape configured to guide the electrode cable into the channel.

5. The cable connecting clip of claim 1, wherein the connecting pad comprises a thermal conductivity control path.

6. The cable connecting clip of claim 5, wherein the thermal conductivity control path comprises a neck section between the connecting pad and the channel.

7. The cable connecting clip of claim 1, wherein the electrode cable comprises a center conductor, a first insulating layer, an inner shield layer, a second insulating layer, the conductive layer, and a jacketing layer.

8. A printed circuit board assembly (PCBA) system included in a wearable cardioverter defibrillator (WCD) comprising:
    an electrode cable having a signal conductor and a first conductive layer;
    a substrate having a first conductive region and a second conductive region; and
    a first conductive clip having a pad section, a saddle section, and a neck section disposed between the pad section and the saddle section, the neck section being narrower than the pad section and the saddle sections, wherein:
        a first portion of the electrode cable is disposed in the saddle section of the first conductive clip;
        a portion of the first conductive layer of the electrode cable being soldered to the saddle section of the first conductive clip, the pad section of the first conductive clip being soldered to the first conductive region of the substrate to electrically couple the portion of the first conductive layer of the electrode cable to the first conductive region of the substrate, and
        the signal conductor of the electrode cable being soldered to the second conductive region of the substrate.

9. The PCBA system of claim 8 further comprising a second conductive clip having a pad section, a saddle section, and a neck section disposed between the pad section and saddle section, wherein:
    a second portion of the electrode cable is disposed in the saddle section of the second conductive clip,
    the electrode cable comprises a second conductive layer, wherein a portion of the second conductive layer of the electrode cable being soldered to the saddle section of the second conductive clip, and
    the pad section of the second conductive clip being soldered to the second conductive region of the substrate to electrically couple the portion of the second conductive layer of the electrode cable to the second conductive region of the substrate.

10. The PCBA system of claim 8, wherein the saddle section comprises a thermal mechanical compensating structure.

11. The PCBA system of claim 10, wherein the thermal mechanical compensating structure comprises a slot, the slot having a predetermined dimension to compensate for thermal mechanical changes of the first conductive clip.

12. The PCBA system of claim 8, wherein the saddle section comprises the saddle section having a substantially "V" type shape configured to guide the electrode cable into the saddle section.

13. The PCBA system of claim 8, wherein the pad section and the neck section are configured to form a thermal conductivity control path.

14. The cable connecting clip of claim 1, wherein the conductive layer is an electrical noise shielding layer.

15. The cable connecting clip of claim 7, wherein the connecting pad is electrically isolated from the inner shield layer.

16. The PCBA system of claim 8, wherein the first conductive layer is an electrical noise shielding layer.

17. The PCBA system of claim 8, wherein the first conductive region comprising a conductive shield pad.

* * * * *